US00PP31459P2

(12) United States Plant Patent
Hansen

(10) Patent No.: US PP31,459 P2
(45) Date of Patent: Feb. 18, 2020

(54) **X *MANGAVE* PLANT NAMED 'RED WING'**

(50) Latin Name: **x *Mangave* hybrid; *Manfreda* times *Agave***
Varietal Denomination: Red Wing

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/350,922

(22) Filed: Feb. 1, 2019

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt

(57) ABSTRACT

A new and unique x *Mangave* plant named 'Red Wing' characterized by a large mound of broad, fleshy, mostly flat foliage with small flexible cream-colored marginal teeth that become firm and orargish-colored when mature. Foliage is upright to outwardly toward stem with a tendency to arch in maturity. The flowers are upright, a mixture of yellowish-chartreuse and reddish orange formed on stiff, branched stalks. The new plant is suitable for the garden or as a potted plant in the garden or home.

2 Drawing Sheets

Botanical classification: x *Mangave* hybrid; *Manfreda* times *Agave*.
Variety denomination: 'Red Wing'.

STATEMENT REGARDING PRIOR DISCLOSURES UNDER 37 CFR 1.77(B)(6)

The first public disclosure of the claimed plant, in the form of a photograph and brief description on a website operated by Walters Gardens, Inc. on Feb. 1, 2018. The claimed plant was first sold on Feb. 12, 2018 by Walters Gardens, Inc., who obtained the plant and all information relating thereto, from the inventor. No plants of x *Mangave* 'Red Wing' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to the new and distinct x *Mangave* hybrid plant, x *Mangave* 'Red Wing' that was hybridized by the inventor at a wholesale perennial nursery in Zeeland, Mich., USA as a cross between an unnamed proprietary selection between *Manfreda longiflora* (not patented) as the female or seed parent times an unnamed selection of *Agave shawii* (not patented) as the male or pollen parent. The cross was performed on Sep. 17, 2012 and seeds were harvested and sown in early 2013. Through trials at the same nursery the plant was assigned the breeder code 12-71-2. The new plant has been successfully asexually propagated by sterile shoot-tip tissue culture and by basal offsets at the same nursery in Zeeland, Mich. The asexual propagation has been found to produce stable and identical plants that maintain all the unique characteristics of the original plant in multiple generations.

BRIEF SUMMARY OF THE INVENTION x *Mangave* 'Red Wing' differs from its parents as well as all other *Manfreda, Agave* and x *Mangave* known to the applicant. The female parent has foliage that is narrower, thinner in cross section, has smaller marginal teeth and has significant mahogany mottling or spotting on both upper and lower surfaces. The flowers of the female parent are smaller, near white turning to reddish in maturity, with short stamens. The male parent is more upright in habit, slower growing, with foliage that is shorter, more glaucous bluish-green without red, broader, more ovate with larger marginal teeth and larger terminal spines. The nearest comparison plants are 'Mission to Mars' U.S. Plant Pat. No. 29,393, 'Freckles and Speckles' U.S. Plant Pat. No. 30,904 and 'Purple People Eater' U.S. Plant Pat. No. 29,949. 'Mission to Mars' has broader and longer leaves and is larger in habit. 'Freckles and Speckles' has foliage that is longer and has less dense reddish coloration, and the plant matures to flowering faster with petals that are less orange hue and anthers that are more burgundy. 'Purple People Eater' has foliage that is more upright and fleshy, of a greenish-purple with reddish-purple spots and less dense reddish coloration.

The new plant, 'Red Wing', is unique from all of the above cultivars and all *Agave*, x *Mangave* and *Manfreda* known to the inventor by the following combined traits:

1. Large mound of glaucous, densely maculate with reddish spots to nearly solid reddish in high light;
2. Leaf margins have small, flexible, cream-colored marginal teeth that become orangish and firm when mature;
3. Upright flowers on slightly ridged or fluted, upright, branched stalk;
4. Flowers are mixtures of yellowish-chartreuse and reddish orange;
5. Moderate to slow growth rate;
6. Foliage is upright to outwardly toward stem.

BRIEF DESCRIPTION OF THE DRAWING

The photograph of x *Mangave* 'Red Wing' demonstrates the overall appearance of the new plant including the unique traits as a five-year-old plant grown in a container in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
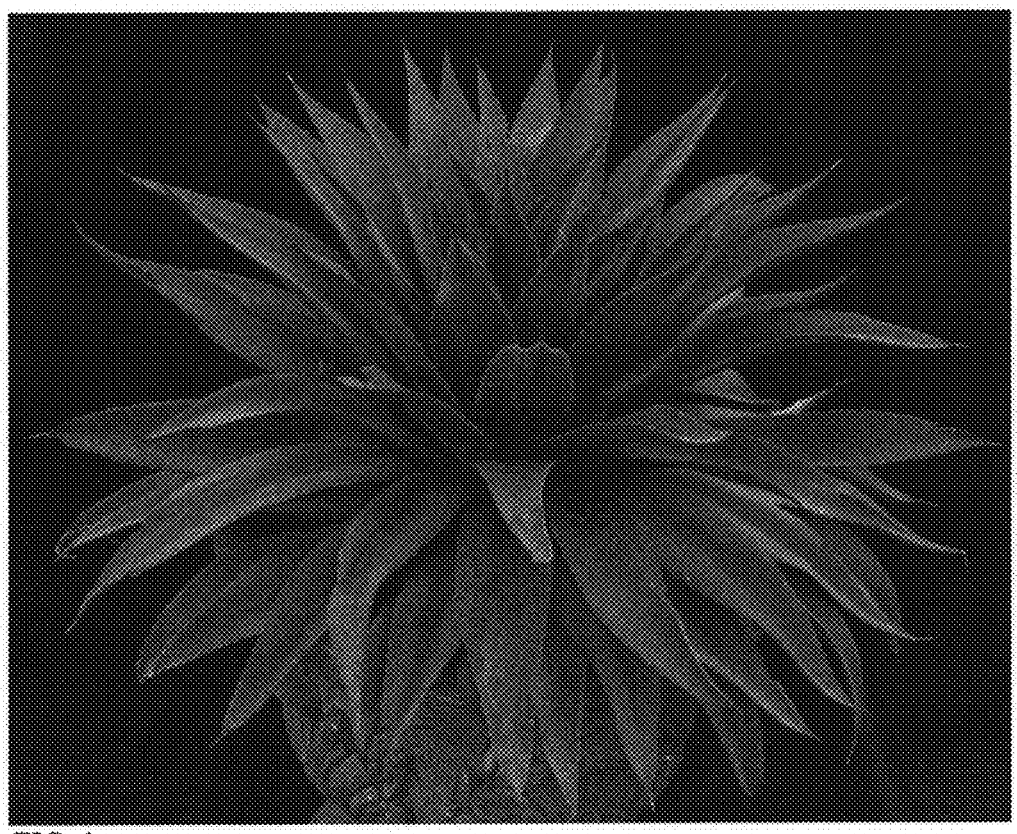
FIG. 1 shows a top view of a five-year-old containerized plant that was grown in a full-sun trial garden.
Figure 2:
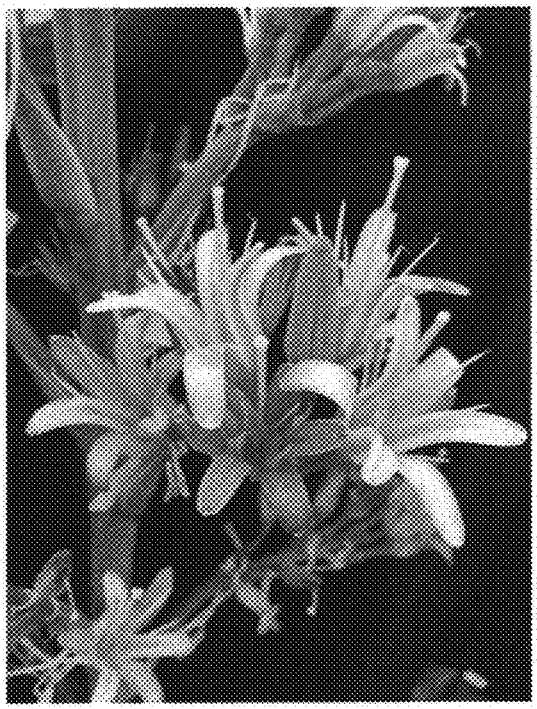
FIG. 2 shows a close-up of the flowers of various ages with stamens removed to prevent self-pollination in hybridizing.
Figure 3:
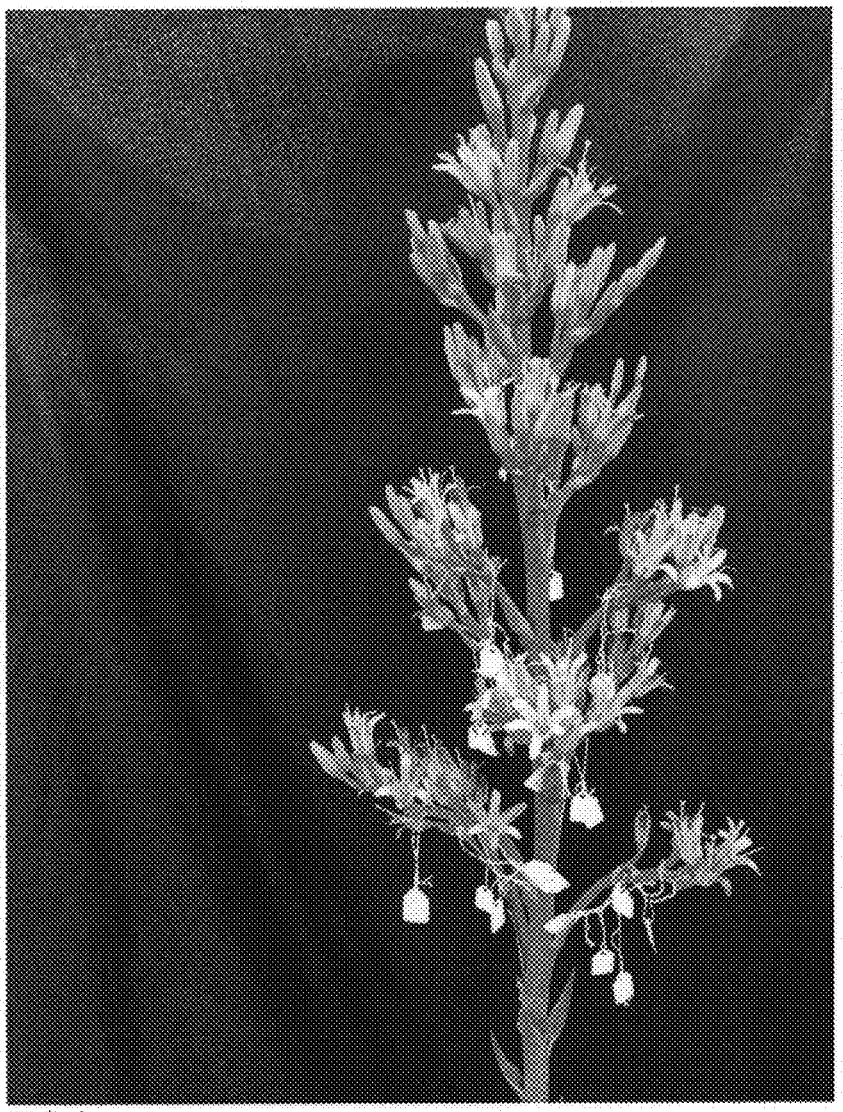
FIG. 3 shows the upper portion of the flower stalk in early stages of flowering.

The following descriptions and color references are based on the 2015 edition of The Royal Horticultural Society Colour Chart except where common dictionary terms are used. The new plant, x *Mangave* 'Red Wing', has not been observed under all possible environments. The phenotype may vary slightly with different environmental conditions, such as temperature, light, fertility, moisture and maturity levels, but without any change in the genotype. The following observations and size descriptions are of a five-year-old plant in a commercial wholesale greenhouse and in a full-sun trial garden in Zeeland, Mich. with supplemental water and fertilizer as needed.

Parentage: An unnamed select form of *Manfreda longiflora* as female or seed patent and an unnamed selection of *Agave shawii* as the male or pollen parent;

Propagation: By sterile shoot-tip tissue culture;

Time to initiate roots from tissue culture: About 21 days;

Growth rate: Moderate to slow;

Crop time: About 16 to 20 weeks to finish in a 3.8 liter container from a 35 mm tissue culture growing at about 21° C.;

Rooting habit: Fleshy, lightly branching, with roots up to 30 cm long;

Root color: Nearest RHS 158C;

Plant shape and habit: Succulent herbaceous perennial with basal rosettes of about 120 leaves radially emerging outwardly from central stem prior to flowering, producing a radially-symmetrical, rounded mound;

Plant size: Foliage height about 45.0 cm tall from soil line to the top of the leaves and about 79.0 cm wide at the widest point about middle of the plant;

Foliage description: Lanceolate; simple; sessile; bi-laterally symmetrical; sarcous; apex narrowly acute with terminal spine; base truncate; mostly flat with flat margins; margins finely dentate; glabrous abaxial and adaxial; glaucous abaxial and adaxial; dull becoming slightly lustrous adaxial and abaxial;

Marginal teeth: With small flexible teeth that become firm with maturity; about 2.0 mm long and 2.0 mm wide at base; about 9.0 mm apart in center on mature leaves;

Terminal spine: Firm; to about 15.0 mm long and 2.5 mm wide at base; color nearest RHS 180B;

Leaf size: To about 37.0 cm long, about 7.5 cm wide toward base; center base about 15.0 mm thick at basal midrib; average about 35.0 cm long, 7.0 cm wide and 5.0 mm thick in longitudinal center;

Foliage fragrance: None observed;

Leaf number: About 120 per plant;

Leaf blade color:

*Adaxial* (*mature*).—In lower ultraviolet light nearest RHS 138B irregularly mottled or maculate distally with nearest a blend between RHS N187B and RHS N186C, proximally and between spots nearest RHS 183C; in high ultraviolet light nearest blend between RHS N77B and RHS N186D.

*Abaxial* (*mature*).—In lower ultraviolet light nearest RHS 138C; in high ultraviolet light nearest blend between RHS N77B and RHS N186D.

*Adaxial* (*young*).—Nearest RHS 137C.

*Abaxial* (*young*).—Nearest RHS 137C.

*Marginal teeth*.—Nearest RHS 155D when young at base becoming between RHS 166B and RHS 166C with maturity in high light.

*Terminal spine*.—Nearest RHS 166A.

Petiole: Leaves sessile;

Veins: Parallel; not distinct abaxial or adaxial;

Inflorescence description: Cylindrical with shallow fluting distally; stiff, ridged, upright, branched panicle; glaucous; glabrous; to about 178.0 cm tall and 2.5 cm diameter at base; about 22 braches before first branch; about 12 branches to about 17.0 cm long and 10.0 mm diameter at base;

Cauline leaves: About 22 per scape before branches; lanceolate; simple; fleshy; glaucous; glabrous; margins finely dentate with flexible teeth; apex narrowly acute with flexible mucro; base truncate, sessile, clasping; proximally about 21.0 cm long and about 2.2 cm wide at base, decreasing distally; color adaxial and abaxial nearest RHS 137C with margins lightening to nearest RHS 155A;

Buds one day prior to opening: Elongated globose; about 4.2 cm long and about 8.0 mm across at mid-tepal, base about 4.0 mm diameter;

Bud color: Nearest RHS 146C with blushing of nearest RHS 173A in tepal portion and proximally nearest RHS 137C;

Flower description in greenhouse conditions: Perfect, actinomorphic; about 7.5 cm long and opening to about 4.3 cm across at outside of anthers and 8.0 mm diameter at ovary; lasting about 3 to 4 days per flower; flowering period about three weeks in late fall or winter in Michigan greenhouse; producing abundant nectar; approximately 110 flowers per scape; attitude mostly upright;

Flower fragrance: Not detected;

Tepals: Six in two sets of three; glaucous abaxial and slightly lustrous adaxial; glabrous both adaxial and abaxial; acute apex and fused base; outer set about 5.5 cm long, fused in about basal 3.0 cm and about 7.0 mm wide at base; inner set about 5.5 cm long and 6.5 mm wide at fusion; inner set creased along edge where overlapped with outer set while in bud;

Tepal color: Variable; young adaxial outer tepal base nearest RHS 145C, middle and distal nearest RHS 145C lightly blushed with nearest RHS 53A; young abaxial outer tepal base nearest RHS 146C, middle blend between RHS 145D and RHS 146D with mixture of RHS 161C and blushed with RHS 178A, apex nearest RHS 187A; young adaxial inner tepal base nearest RHS 145C, margin nearest RHS 150D, distal blushed with nearest RHS 183C; young abaxial inner tepal base nearest RHS 145A, middle margin nearest RHS 150D, distal center lightly blushed with nearest RHS 187C, distal margin nearest RHS 160D with light blushing of nearest RHS 187C; mature adaxial outer and inner tepal base nearest RHS 146B, middle nearest RHS 160D with heavy blush of nearest RHS 183A and apex nearest RHS 183A; mature abaxial outer and inner tepal base nearest RHS 146D, middle RHS 146D blushed with nearest RHS 183C and apex nearest RHS 183B;

Androecium: Six;

*Filaments*.—Six; cylindrical distally, slightly applanate base; stiff and straight; about 3.0 cm long and 1.5 mm diameter at base; color between RHS 145D and RHS 150D.

*Anther*.—Dorsifixed; longitudinal; about 1.0 cm long and 2.0 mm diameter before opening; after dehiscence curving backward; color nearest RHS 11B.

*Pollen*.—Abundant; color nearest RHS 11A.

Gynoecium: Single; 78 mm long;

*Style*.—6.0 cm long and 1.5 mm diameter at base; color between RHS 150D and RHS 185D.

*Stigma*.—Turbinate, apex tri-lobed; about 2.0 mm tall and 2.0 mm across top; color nearest RHS 11C.

*Ovary*.—Inferior; to 19.0 mm long and 8.0 mm wide; color nearest RHS 137C.

Peduncle: Flowering in upper 80.0 cm to about 25.0 cm wide; with about eleven branches; branches held upright at about a 45 degree angle above horizontal, to about 17.0 cm long and 10.0 mm diameter;

Peduncle color: Nearest RHS 138A;

Fruit: Dehiscent, tri-valved, loculicidal capsule; apex broadly acute with 2.0 mm long terminal; base slightly tapered; about 3.0 cm long and 2.0 cm across;

Fruit color: When immature nearest RHS N138A; pods have not yet dehisced;

Seed: Have not yet been harvested;

Disease resistance: X *Mangave* 'Red Wing' has not been observed to be resistant to diseases beyond that which is normal for x *Mangave, Agave* or *Manfreda*. The new plant is xeromorphic and survives well with minimal water once established. The new plant is estimated to be hardy at least from USDA zone 9. Full extent of winter hardiness has not been tested.

It is claimed:

1. A new and distinct cultivar of ornamental x *Mangave* plant named 'Red Wing' as herein described and illustrated.

* * * * *